United States Patent [19]

Ware

[11] Patent Number: 5,086,773
[45] Date of Patent: Feb. 11, 1992

[54] TOOL-LESS PACEMAKER LEAD ASSEMBLY

[75] Inventor: Lyle A. Ware, Albuquerque, N. Mex.

[73] Assignee: Cardiac Pacemakers, Inc., St. Paul, Minn.

[21] Appl. No.: 580,169

[22] Filed: Sep. 10, 1990

[51] Int. Cl.⁵ ............................................. A61N 1/05
[52] U.S. Cl. ................................. 128/419 P; 128/784
[58] Field of Search ........................ 128/419 P, 784

[56] References Cited

U.S. PATENT DOCUMENTS

| | | |
|---|---|---|
| 317,887 | 5/1885 | Thompson . |
| 1,259,007 | 3/1918 | Fifield . |
| 2,427,007 | 9/1947 | Lambach . |
| 3,058,083 | 10/1962 | Schneider . |
| 3,380,017 | 3/1980 | Gomulka ........................ 339/75 M |
| 3,822,707 | 7/1974 | Adducci et al. ................. 128/419 P |
| 3,908,668 | 9/1975 | Boldue ............................ 128/419 P |
| 4,000,745 | 1/1977 | Goldberg ........................ 128/418 |
| 4,027,678 | 6/1977 | van Oostveen et al. ........ 128/419 P |
| 4,072,154 | 2/1978 | Anderson et al. .............. 128/419 P |
| 4,192,567 | 4/1968 | Gomolka . |
| 4,461,194 | 7/1984 | Moore ............................ 128/419 P |
| 4,532,931 | 8/1985 | Mills .............................. 128/419 PG |
| 4,655,771 | 4/1987 | Wallsten ........................ 623/1 |
| 4,703,149 | 10/1987 | Sugisawa et al. ............ 219/10.55 E |
| 4,796,776 | 1/1989 | Dalquist et al. ............... 220/203 |

Primary Examiner—William E. Kamm
Assistant Examiner—Scott M. Getzow
Attorney, Agent, or Firm—Haugen and Nikolai

[57] ABSTRACT

A lead connection assembly for an implantable device forming a subcutaneous electrical and mechanical connection with an electrical lead without tools employs connectors in the form of a resilient conductive spring-retainers each in the shape of a generally cylindrical helix disposed in a bore for receiving the lead. Each spring retaining connector is electrically connected to the internal circuitry of the implantable device using a feedthrough connection and the helix of the retaining connector means is adapted to receive a terminal poriton of the lead. The helix operates in a manner such that when the lead is rotated a partial revolution within the helix in a direction, which would tend to unwind the helix, the lead is simultaneously freed to move axially in and out of the helix coil and when the lead is rotated a partial revolution within the helix in a direction which tends to tighten the helix winding, the coil permanently seizes the lead such that it cannot be withdrawn without first being rotated in the unwinding direction.

7 Claims, 2 Drawing Sheets

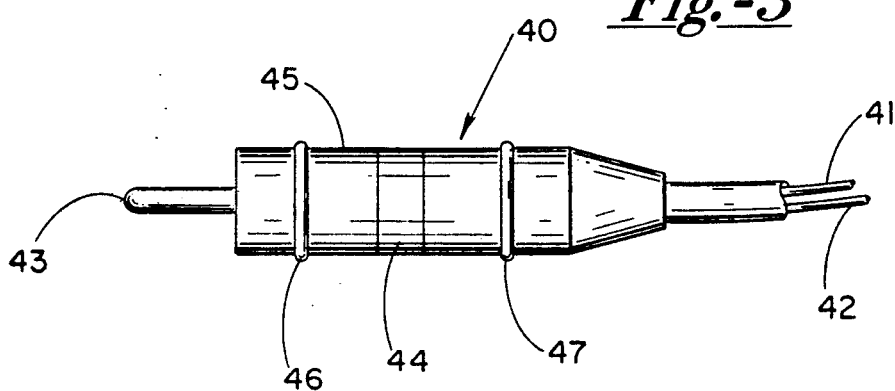
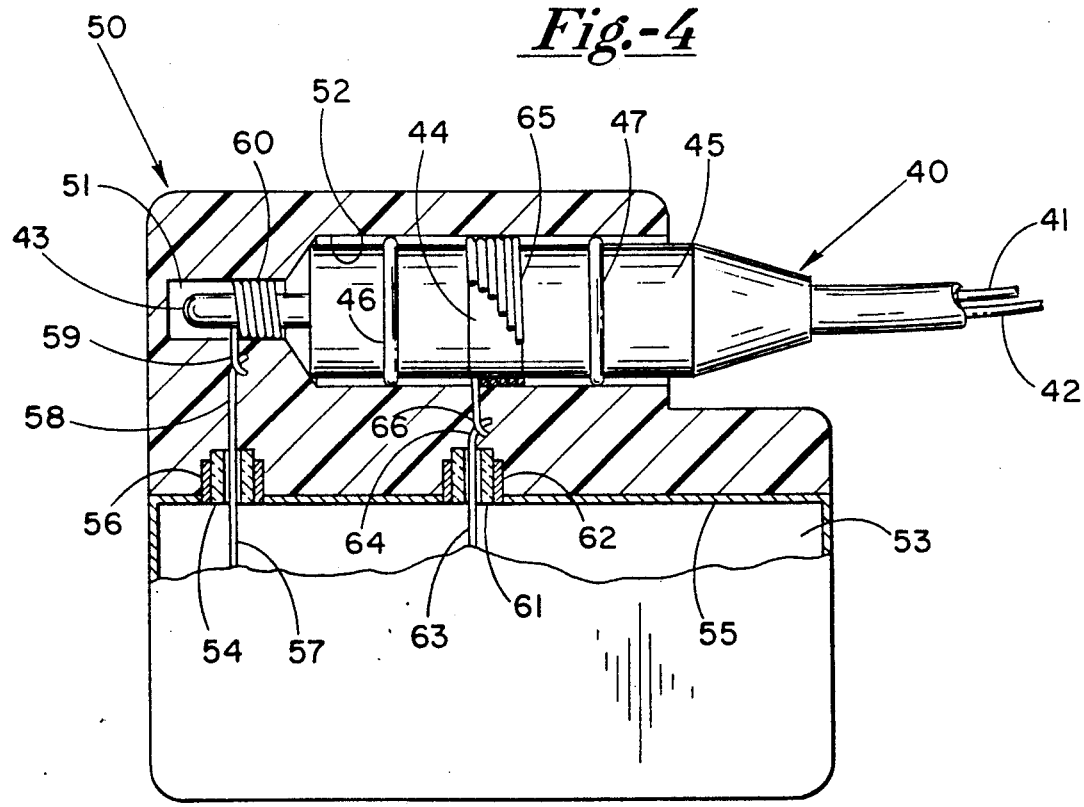

TOOL-LESS PACEMAKER LEAD ASSEMBLY

BACKGROUND OF THE INVENTION

I. Field of the Invention

The present invention is directed generally to implantable body organ stimulators and, more specifically, to a system for connecting electrical lead to implanted electrical stimulus generating devices without having to access these connections directly with tools, or the like, to effect the connection or disconnection.

II. Description of the Related Art

Certain particularly useful medical treatment systems involve devices chronically implanted in the body that deliver pulses of electrical energy to stimulate or otherwise affect proximate body tissue. An exemplary device of this type, and one which is probably the best known, is the cardiac pacer which includes a pulse generator having a power source and electrical circuitry for generating timed electric pulses to stimulate designated heart muscles. The pulses are delivered through electrically conductive leads having proximal end terminals connected to the pulse generator and one or more unipolar or bipolar distal end electrodes secured to the myocardial tissue at the situs of interest for stimulation at a location remote from the pulse generator itself.

The defibrillator is a further example of a more recent implantable stimulating device. That system is designed to terminate arrhythmias such as ventricular fibrillation or tachycardia, by application of one or more properly timed electrical pulses to the appropriate part of the heart. The defibrillator differs from the pacer in that the electrical pulses involved are of much greater intensity and are delivered only in response to sensing arrhythmias or abnormalities of a certain degree. Other devices, e.g., neuromuscular stimulators, also involve implantable means for delivering electrical impulses through leads from a pulse generator through leads to stimulate tissue.

With respect to such devices, generally, the term "pulse generator" refers to the implantable electronic source device which controls and generates the stimulus, while the term "lead" refers to the insulated conductive wire (or wires) which are electrically and mechanically coupled to the pulse generator and which receive each stimulating impulse from the pulse generator and transmit each impulse to the heart or organ of interest. The lead incorporates at least one electrode which is the conductive element or contact normally exposed or adjacent the distal end of the lead to establish electrical contact with the tissue of interest, such as the heart muscle.

In the case of an implantable cardiac pacer system, either endocardial leads or myocardial leads may be employed. Endocardial leads are internal leads to the heart which enter the heart through a vein and make contact with the endocardium while myocardial leads are those which are attached to the external surface of the heart having an electrode making contact with the myocardium. Established surgical procedures developed and perfected over time are employed for the lead placement with respect to the tissue. These procedures are well known in the art and need not be further treated here. Following placement of lead electrodes, thresholds are determined. Upon indication of satisfactory thresholds, the proximal leads are connected to the pulse generator which is also chronically implanted at a distance from the heart.

The connection of the electrode lead or lead assemblies to the pulse generator has traditionally been accomplished by the insertion of the exposed terminal pin of the lead into a connector block located in a housing attached to but separate from the main chamber of the pulse generator. Inasmuch as the terminal pin and the connector block have exposed conductive surfaces, it also has been necessary for the zone surrounding the terminal pin-connector block to be sealed and maintained free of body fluids. Leakage of body fluids into the cavity or zone occupied by the terminal pin-connector block combination may adversely affect pacer performance. Thus, the system requires a fluid-tight housing and a connection which preserves electrical integrity.

The procedure for inserting the leads into the pulse generator must be one which can be accomplished with a maximum degree of freedom to avoid inadvertent moving of the placed electrode and lead. Of course, in turn, this requires that the procedure for inserting the terminal pin and securing connection of the lead assembly into the connector block be accomplished as easily as possible.

Normally, the lead is generally cylindrical and may have one or more additional sequential axial segments of increasing diameter. The assembly may have a tip (or pin) terminal or both a pin and a ring terminal accessible on that portion of the lead which is received within the connector housing on the body of the pulse generator. The lead connector is durable and rigid and the terminals are axially spaced inward from a seal between the connector housing of the pulse generator and the environment.

Heretofore, the terminal pins have been inserted into a connector block integral with the body of the connector housing and held in place utilizing set screws. Manipulation of a set screw requires that a tool be inserted from outside the body to address the subcutaneously located pulse generator body at a location spaced from the insertion opening in the connector housing in order to accomplish the tightening of the set screw in the connector block to secure the terminal pin in place. A resilient sealing plug is normally installed over the set screw to effect a fluid tight, electrically insulating seal.

Such known means for connecting leads to body implantable devices are exemplified by U.S. Pat. No. 4,461,194 to Moore, in which the seal plug is positioned between the set screw and a cap; U.S. Pat. No. 4,072,154 to Anderson, et al. utilizes a seal plug in conjunction with a set screw to positively retain the lead. Many other similar techniques are used for such devices, all of which require rather traumatic surgical procedures to accomplish any connection or disconnection of the leads to the body of the pulse generator.

In addition, all of these connection techniques require specialized tools which, as a practical matter, are easily misplaced as they are relatively small and not often used; and they are difficult to maintain in a sterile condition. The small parts, such as plugs and set screws, can also easily be misplaced, even within surgical openings in patients.

From the above, it is evident that there has been a continuing need for a simpler approach to connecting and disconnecting the proximal leads of such devices through the connector housing on the body of the pulse generator. Such an approach would eliminate the need for separate small parts and specialized tools. Accordingly, it is a primary object of the present invention to accomplish the connection and disconnection of the proximal ends of subcutaneous electrode lead assemblies of electrically stimulating implanted electrodes to the implanted body of a pulse generator without additional parts or specialty tools.

Another object of the present invention is to connect and disconnect the proximal ends of such leads with minimal need for surgically invasive procedure.

A still further object of the present invention is to accomplish the connecting and disconnecting of the proximal lead assembly ends of in a manner which, though tool-less, is simple, and easy, and which provides a positive and reliable connection.

SUMMARY OF THE INVENTION

In accordance with the present invention, connection of the proximal ends of lead assemblies to body implanted pulse generating devices such as cardiac pacers is accomplished in a simplified, reliable manner with minimal need for invasive surgical procedures to access the site and without the need for the insertion of tools. In order to effect positive connection or disconnection of the leads utilizing the lead connecting system of the present invention, one need only be able to access the connection port or bore in the pulse generator housing and accomplish minor manipulation of the proximal end of the lead assembly to the connect it to the implanted pulse generating device. The invention contemplates the connection of one or more leads having pin, ring, pin and ring, or a pin and multiple ring type terminals a generally cylindrical plug-in type proximal lead end assembly.

In the preferred embodiment, longitudinal concentric bores are provided in a housing attached to the main chamber of the pulse generator, a first or pin terminal receiving bore is combined with a coaxial second bore having a diameter greater than the first bore but which opens to the exterior surface of the connector block housing and is adapted for receiving a second or larger cylindrical portion of the electric lead having a diameter greater than the tip portion and carrying a ring terminal connector. Both mechanical and electrical connection of the pin and/or ring connectors is achieved utilizing one or more resilient conductive spring retaining connector members having a spring generally in the shape of a cylindrical helix.

In the case of the pin terminal, the spring member is fixed in the first bore and an extension of the spring in the form of a straight segment provides the electrical connection via a feedthrough system to the internal circuitry of the implanted pulse generating device through an hermetically sealed opening to the main pulse generator chamber. The helix of the retaining conductor member's spring is adapted to receive the cylindrical pin portion of the lead and, in its normal or relaxed position, has a diameter very slightly smaller than the outside diameter of the member to be contained. When the lead assembly is rotated a partial revolution within the helix in the direction which would tend to unwind the helix, the cylindrical lead becomes free to move longitudinally in and out of the helix coil and when the lead is rotated a partial revolution within the helix in the opposite direction which tends to tighten the helix winding, the coil permanently seizes the lead such that it cannot be withdrawn without first being rotated to at least a slight degree in the unwinding direction again.

Spring connectors also can be provided for one or more ring terminals, if such be used, which operate in the same manner as that provided for the tip terminal. Leads having both tip and ring terminals can be retained by either one or more springs, a plurality of springs being preferred such that all electrical connections are made easily and in the same manner. In a two-spring or multi-spring version, all springs operate to mechanically grip the lead assembly in the same manner as the single spring such that a minor rotation of the lead can accomplish fixation of the lead via all springs within the connecting housing and a slight rotation in the opposite direction can free the lead for quick disconnect and withdrawal from the connector housing.

Direct access is required only to provide the minor twist and insertion or withdrawal manipulations to the lead terminals necessary for connecting and disconnecting to the connector block housing and to assure proper sealing of the system. It has been found that this system works very well with any type of rigid, cylindrical leads and the spring can be adapted for use with any diameter lead to accomplish both positive connection of the lead and excellent electrical contact.

BRIEF DESCRIPTION OF THE DRAWINGS

In the drawings, wherein like numerals are utilized to designate like parts throughout the same:

FIG. 3 illustrates a typical lead having pin and ring terminals; and

FIG. 4 is a side elevational view of a pulse generator similar to that shown in FIG. 1 with parts cut away showing the lead connecting system of the invention.

DETAILED DESCRIPTION

The detailed description depicts one or more specific forms of the present invention based on the several drawing figures provided. This is meant to illustrate the nature of the invention rather than to limit the scope of that invention and it is contemplated that other forms or variations might occur to those skilled in the art. This, of course, includes applications and adaptations of the invention to chronic subcutaneously mounted devices other than cardiac pacers.

Figure 1:
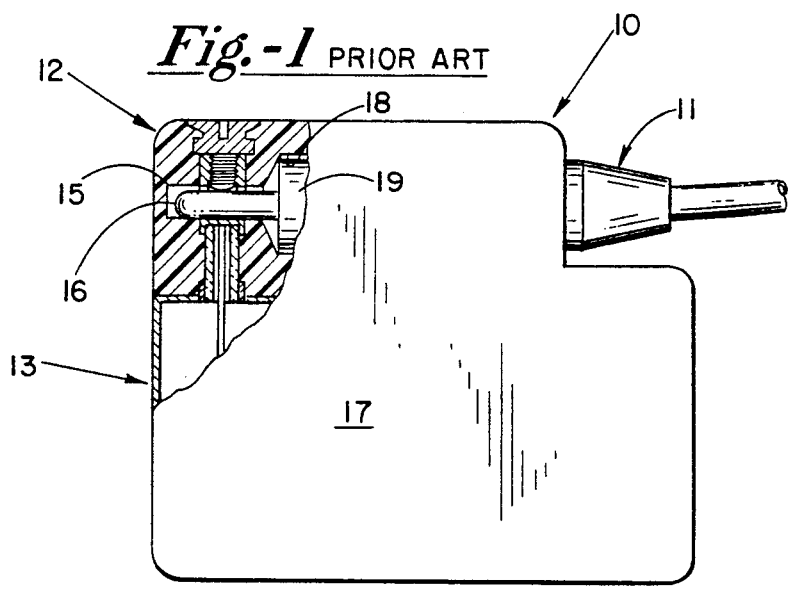
FIG. 1 is a side elevational view, with parts cut away, illustrating a prior art pulse generator with the proximal tip or pin end of the lead assembly connected into the connector block of the pulse generator.

FIG. 1 depicts a cardiac pacer apparatus generally at 10 including a lead assembly shown in part at along with a connector housing 12 and a pulse generator body shown in part as including the enclosure at 13. The lead assembly further consists of an elongated generally tubular structure having one or more insulated conductive elements as at 14 (FIG. 2) disposed within the lumen of the tube in a well known manner. Likewise, the distal end of the probe (not shown) contains an electrode connected to each such conductive element and adapted for placement in the tissue of interest in a well known manner. The details of the lead assembly especially with regard to placement and anchoring of the unipolar or bipolar electrodes in the heart tissue are well known and need not be treated in greater detail here.

The connection housing consists of an housing member 12 which is composed of a biocompatible electrically insulating material, normally epoxy, and which is fixed to the enclosure 13 of the pulse generator. The assembly is covered by a further biocompatible overlayer as at 17, which also may be epoxy, suitable for long-term or chronic implantation. The epoxy member 12 has a first bore 15 formed therein to receive the proximal pin end terminal 16 of the lead assembly 11. Longitudinally sequentially coaxial with the bore 15 is a rather larger bore 18 designed to accommodate the larger diameter segment 19 of the lead assembly 11. Thus, the lead assembly 11 includes dual generally closed cylindrical segments 16 and 19 arranged generally coaxially with the conductive elements, as at 14, with the conductive element 14 terminating in the segment 16 which also serves as the pin terminal for the connection.

Figure 2:
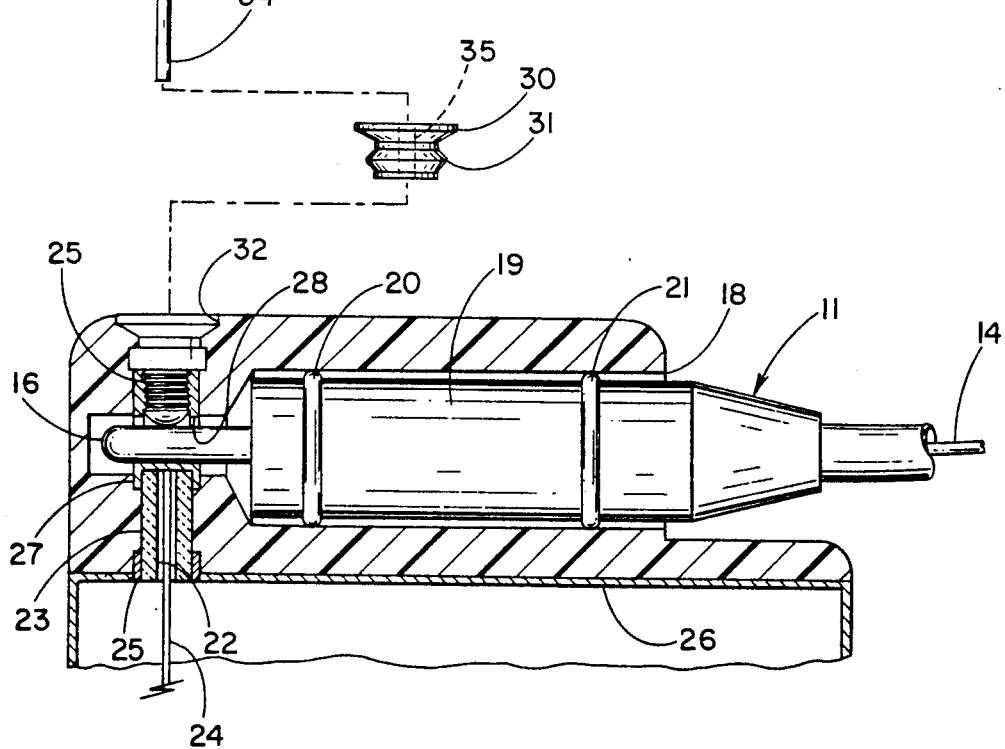
FIG. 2 is a partial vertical sectional view of the pulse generator of FIG. 1 on a slightly enlarged scale, illustrating in greater detail the manner in which the lead assembly is received within the bore of the connector housing of the pulse generator, and illustrating a plug seal component and a tool for inserting a set screw and the plug seal shown in exploded disposition relative to the pulse generator.

As better seen in FIG. 2, sealing means are provided between the lead assembly 11 and the larger bore 18 by means of sealing rings 20 and 21 which is typically of semicircular cross-section resembling, in section, half of an O-ring. The lead assembly 11 is fixed in the epoxy member 12 utilizing a terminal block system such as that illustrated in FIGS. 1 and 2. The housing member 12 is provided with a bore designed to accommodate an insulating sleeve member 23, which may be a ceramic sleeve member. The ceramic sleeve member 23 itself has an internal bore 22 adapted to receive and accommodate a feedthrough conductor such as that illustrated at 24 which is designed to be hermetically sealed in the ceramic sleeve 23 to connect the internal circuitry of the pulse generator with the tip terminal of the lead assembly. Additional strength and sealing may be added by employing an additional metal sleeve member, such as that shown at 25, which may be bonded hermetically about the outer periphery of the ceramic sleeve 23 and may also be sealingly and permanently attached as by brazing to the top wall 26 of the enclosure 13. A second conducting member 27 is located adjacent the upper end of the sleeve 23 and provides further means for receiving the pin terminal in conductive relation with conductor 24 in sleeve member 23. The block sleeve member 28 is fixed in the housing 12 and contains openings to accommodate the pin terminal 16 of the lead assembly 11 and a set screw 29 threadably received within the bore of the sleeve 28 is utilized to lock the pin member in place such that the lead assembly 11 cannot be withdrawn from the dual bore. When the set screw 29 is tightened, of course, the pin terminal 16 is electrically connected with the feedthrough conductor 24 which is permanently attached and sealed to the inside of the insulating sleeve 23.

A resilient plug seal 30 is utilized to achieve a fluid tight seal between the external body fluid environment and the internal cavity of the housing member 12 in a well known manner, the diameter of the plug member at 31 being larger than the diameter of the bore at 32. A tool is illustrated at 33 which may be utilized to rotate the set screw 29 to tighten or loosen the connection of the lead assembly 11. The plug member 30 may also be of the resilient self-sealing variety in which the tip 34 of the tool 33 penetrates a resilient self-sealing opening 35 in the plug 30 to operate the set screw 29. When the tool is withdrawn, the resilient plug material recloses the opening in a fluid-tight mode.

As can be seen from FIGS. 1 and 2, the prior system may require external access to remove or install a plug member 30 and does require access to loosen or tighten the set screw 29 in order to connect or disconnect the lead assembly 11 from the connector block. In addition, access must be had to the insertion and removal area at the opposite end of the device when inserting or removing the lead assembly 11.

FIG. 3 illustrates a cylindrical lead assembly generally at 40 carrying a plurality of insulated electrode conductor members as at 41 and 42. An external tip or pin terminal 43 and ring terminal connector 44 are also illustrated. The diameter of the tip cylinder 43 is notably smaller than the ring carrying segment 45. A pair of sealing rings 46 and 47, which may operate in the same manner as sealing rings 20 and 21 in FIGS. 1 and 2, are also shown.

FIG. 4 illustrates the attachment of the lead assembly 40 into a pacer system in accordance with the present invention. In this manner, a biocompatible, insulating connection housing member is provided at 50, which may be epoxy, and which is provided with concentric axially aligned, longitudinally placed bores 51 and 52 designed to accommodate the pin terminal 43 and the larger bore cylinder 45, including the ring terminal 44. The tip terminal 43 is connected electrically to the internal circuitry of the pulse generator in chamber or compartment 53 via a feedthrough system.

The feedthrough system includes ceramic or other rigid, nonconducting hollow sleeve as at 54 defining a bore which is aligned with an access opening in the shell or partition member 55 of the pulse generator compartment 53. As was the case in FIG. 2, a metal sleeve member as at 56 may be bonded hermetically about the outer periphery of the ceramic sleeve 54 and brazed or otherwise sealed to the metallic enclosure top member 55. Such a reinforcing member also can be extruded from the metallic top member 55 during its formation from sheet metal. A feedthrough conductor member 57 is hermetically sealed in the hollow sleeve 54, as by filling the hollow sleeve 54 with brazing material, and connects at one end to internal circuitry of the pulse generator in a well-known manner (not shown) and, at the other end, extends as 58 to contact extension 59 of resilient retaining spring 60 (discussed below). Likewise, hollow sleeve 61 addresses an opening to connect through the member 55 to the internal workings of the pulse generator. Sleeve 61 may be further reinforced by metal retainer sleeve 62 provided in a manner previously discussed. A feedthrough conductor 63 is also hermetically sealed in sleeve 62 and is extended at 64 to engage the extension 66 of resilient retaining spring 65.

In accordance with the present invention, the quick and easy positive connection between the lead assembly 40 and the connection block assembly is accomplished by the use of generally cylindrical, helical resilient conductive retaining spring connectors 60 and 65, both of which are resilient metallic members which, at the same time, provide excellent electrical conduction. They are continued in respective extension segments 59 and 66, which connect to respective feedthrough conductor member extensions 58 and 64. The inside surfaces of the hollow sleeves 54 and 61 may be silvered or otherwise made conductive to aid in achieving good feedthrough electrical contact.

The generally cylindrical helix-shaped spring connector members generally describe an internal diameter minutely smaller than the external diameter of the pin terminal 43 or cylinder 45 and ring 44 and cooperate with the corresponding portions of the generally cylindrical proximal lead assembly in a manner such that when the terminal is inserted into the spring loaded bore system and is rotated a small amount (which only need be a fraction of a revolution) in the direction which tends to unwind the spring coil of the cylindrical helix it allows free axial passage of the cylindrical portions 43 and 45 to be pushed in through the respective spring members 60 and 65 until the terminal lead is properly positioned within the bore. A slight rotation in the opposite direction which tends to tighten the coil of the helix of the spring causes the spring members to grab the proximate corresponding cylindrical portion of the proximal lead resulting in a tight positive connection which maintains until the lead is again rotated in the loosening direction at which time it can again easily be simultaneously pulled out axially and removed from, or repositioned longitudinally in, the bore.

The system of the present invention allows the proximal terminal lead assembly to be inserted and withdrawn with just a slight revolution of the pin and has been found to provide an excellent mechanical and electrical connection with respect to chronic implants. The diameter of the wire member of the spring itself together with the desired number of coils utilized for the connection depends on the relative size of the members being connected and the amount of electrical current being conducted through the system. This together with the helix diameter and the tension in the spring can be varied according to each application as necessary. With respect to cardiac pacer leads having a pin terminal diameter of approximately 0.060 inch and a ring terminal diameter of approximately 0.100 inch, resilient wire springs of stainless steel having a nominal wire diameter of approximately 0.015 inch (15 mil) have been found to be quite successful.

In accordance with the present invention, the positive retention of the lead assembly 40 is accomplished in a manner which allows for quick connection and disconnection without the use of tools through a very small opening and accomplishes excellent electrical connection where required. Of course, the proximal end of the lead assembly may have a tip or pin terminal, a ring terminal, both a pin and ring terminal or a pin terminal with a plurality of ring terminals. It has further been found, however, that utilizing the spring connector of the invention, solely on the pin or on the ring connection alone, will suffice to produce sufficient mechanical connection for the assembly.

This invention has been described herein in considerable detail in order to comply with the Patent Statutes and provide those skilled in the art with the information needed to apply the normal principles and to construct and use such specialized components as are required. However, it is to be understood that the invention can be carried out using modifications of the embodiments illustrated and specifically with regard to other similarly situated devices without departing from the scope of the invention itself.

What is claimed is:

1. A lead connection assembly for an implantable device forming a subcutaneous electrical and mechanical connection with an electrical lead without tools comprising:

an electrically insulative housing having a biocompatible exterior surface;

a longitudinal bore in the housing for receiving an electrically conductive terminal tip portion of a generally cylindrical electrical lead;

a connector means in the form of a resilient conductive spring retaining connector means in the shape of a generally cylindrical helix disposed in the bore, the spring retaining connector means further being adapted to be electrically connected to the internal circuitry of the implantable device, the helix of the retaining connector means further being adapted to receive the pin portion of the lead making electrical contact to the conductive pin terminal thereof, the connector means operating in a manner such that when the lead is rotated a partial revolution within the helix in a first direction which would tend to unwind the helix, the lead is freed to move longitudinally in and out of the helix coil and when the lead is rotated a partial revolution within the helix in a second direction which tends to tighten the helix winding, the coil permanently seizes the lead such that it cannot be withdrawn without first being rotated in the first direction; and wherein the insertion of the lead further provides a biocompatible seal accomplishing electrical and fluid isolation of the connector means from bodily fluids proximate the exterior surface of the implantable device.

2. A lead connection assembly for an implantable device forming a subcutaneous electrical and mechanical connection with an electrical lead having pin and ring connectors adapted to be connected and disconnected without tools comprising an electrically insulative housing having a biocompatible exterior surface;

a longitudinal bore in the housing for receiving an electrically conductive terminal tip portion of a generally cylindrical electrical lead;

a longitudinal first bore in the housing for receiving an electrically conductive pin terminal first portion of a generally cylindrical electrical lead;

a longitudinal second bore having a diameter greater than the first bore in the housing open to the first bore and to the exterior surface of the housing for receiving a second cylindrical portion of the electrical lead having a diameter greater than that of the tip portion and carrying a ring terminal connector;

a first connector means in the form of a resilient conductive spring retaining connector in the shape of a generally cylindrical helix disposed in the first bore, the spring retaining connector means adapted to be electrically connected to the internal circuitry of the implantable device, the helix of the retaining connector means further being adapted to receive the pin portion of the lead making electrical contact with the conductive pin terminal thereof, the connection operating in a manner such that when the lead is rotated a partial revolution within the helix in a first direction which would tend to unwind the helix, the lead is freed to move longitudinally in and out of the helix coil and when the lead is rotated a partial revolution within the helix in a second direction, which tends to tighten the helix winding, the coil permanently seizes the lead such that it cannot be withdrawn without first being rotated in the first direction; and wherein the insertion of the lead further provides a biocompatible seal accomplishing electrical and fluid isolation of the connector means from bodily fluids proximate the exterior surface of the implantable device.

3. The apparatus of claim 2 further comprising second connector means in the form of a resilient conductive spring retainer configured as a generally cylindrical helix disposed in the second bore, the second spring retaining conductor means having a terminal adapted to be electrically connected to the implantable device and wherein the helix of the second retaining connector means is adapted to receive the second cylindrical portion of the lead including making electrical contact with the conductive ring terminal thereof.

4. The apparatus of claim 3 wherein the second cylindrical portion of the lead is received in the second resilient conductive spring means in a manner such that when the lead is rotated a partial revolution within the helix in a first direction which tends to unwind the helix, the lead is freed to move longitudinally in and out of the helix coil and when the lead is rotated a partial revolution within the helix in a second direction which tends to tighten the helix winding, the coil of the second connector means permanently seizes the lead such that it cannot be withdrawn without first being rotated at least a partial revolution in the first direction again.

5. The apparatus of claim 4 further comprising additional conductive ring terminals on the electrical lead.

6. A lead connection assembly for an implantable device forming a subcutaneous electrical and mechanical connection with an electrical lead, having pin and ring connectors comprising:
   an electrically insulative housing having a biocompatible exterior surface;
   a longitudinal first bore in the housing for receiving an electrically conductive pin terminal first cylindrical portion of a generally cylindrical electrical lead;
   a longitudinal second bore having a diameter greater than the first bore in the housing open to the first bore and to the exterior surface of the housing for receiving a second cylindrical portion of the lead having a diameter greater than that of the pin portion and carrying a ring terminal connector;
   pin terminal connector means for electrically connecting the tip terminal to the internal circuitry of the implantable device;
   ring terminal connector means in the form of a resilient conductive spring retainer in the shape of a generally cylindrical helix disposed in the second bore, the spring retaining connector means having a terminal electrically connected to the circuitry of the implantable device, the helix of the retaining connector means being adapted to receive the second cylindrical portion of the lead making electrical contact to the conductive ring terminal thereof, the connector means operating in a manner such that when the lead is rotated a partial revolution within the helix in a first direction which would tend to unwind the helix, the lead is freed to move longitudinally in and out of the helix coil and when the lead is rotated a partial revolution within the helix in a second direction which tends to tighten the helix winding, the coil permanently seizes the lead such that it cannot be withdrawn without first being rotated in the first direction; and
   wherein the insertion of the lead further provides a biocompatible seal accomplishing electrical and fluid isolation of the connector means from bodily fluids proximate the exterior surface of the implantable device.

7. A lead connection assembly for an implantable device for forming a subcutaneous electrical and mechanical connection with an electrical lead having a pin and at least one ring connector without the need of tools comprising:
   an electrically insulative housing having a biocompatible exterior surface;
   a longitudinal first bore in the housing for receiving an electrically conductive pin terminal first portion of a generally cylindrical electrical lead;
   a longitudinal second bore having a diameter greater than the first bore in the housing open to the first bore and to the exterior surface of the housing for receiving a second cylindrical portion of the electrical lead having a diameter greater than that of the pin portion and carrying at least one ring terminal connector;
   a first connector means in the form of a resilient conductive spring retaining connector in the shape of a generally cylindrical helix disposed in the first bore, the spring retaining connector means having a terminal being in electrical communication with the circuitry of the implantable device, the helix of the retaining connector means being adapted to receive the tip portion of the lead making electrical contact to the conductive terminal thereof, the first connector means operating in a manner such that when the lead is rotated a partial revolution within the helix in a first direction which would tend to unwind the helix, the lead is freed to move longitudinally in and out of the helix coil and when the lead is rotated a partial revolution within the helix in a second direction which tends to tighten the helix winding, the coil permanently seizes the lead such that it cannot be withdrawn without first being rotated in the first direction; and
   at least one second connector means in the form of a resilient conductive spring retainer in the shape of a generally cylindrical helix disposed in the second bore, the second connector means having a terminal in electrical communication with the implantable device, the helix of each second retaining connector means being adapted to receive the second cylindrical potion of the lead making electrical contact with a respective conductive ring terminal, each second connector means operating in a manner such that when the lead is rotated a partial revolution within the helix in a first direction which would tend to unwind the helix, the lead is freed to move longitudinally in and out of the helix coil and when the lead is rotated a partial revolution within the helix in a second direction which tends to tighten the helix winding, the coil of the second connector means permanently seizes the lead such that it cannot be withdrawn without first being rotated in the first direction; and
   wherein the insertion of the lead further provides a biocompatible seal accomplishing electrical and fluid isolation of the connector means from bodily fluids proximate the exterior surface of the implantable device.

* * * * *